United States Patent [19]

Conroy et al.

[11] Patent Number: 4,870,004

[45] Date of Patent: Sep. 26, 1989

[54] APPARATUS AND METHOD OF ANALYZING NUCLEIC ACID MOLECULES

[75] Inventors: Thomas J. Conroy, Los Angeles; Martin H. Graham, Berkeley, both of Calif.

[73] Assignee: Autoseq, Inc.

[21] Appl. No.: 618,572

[22] Filed: Jun. 8, 1984

[51] Int. Cl.[4] .............................................. C12Q 1/68
[52] U.S. Cl. ........................................ 435/6; 436/162;
935/85; 935/86; 935/87; 204/182.3; 204/182.7;
204/182.8; 204/182.9; 204/299 R; 210/243;
422/70
[58] Field of Search ............ 204/299 R, 180 R, 182.3,
204/182.7, 182.8, 182.9; 935/85, 86, 87; 435/6;
210/243; 422/70; 436/162

[56] References Cited

U.S. PATENT DOCUMENTS

| | | | |
|---|---|---|---|
| 4,154,669 | 5/1979 | Goetz | 204/299 R |
| 4,375,401 | 3/1983 | Catsimpoolas | 204/299 R |
| 4,456,513 | 6/1984 | Kawai et al. | 204/299 R |
| 4,545,888 | 10/1985 | Walsh | 204/299 R |
| 4,729,947 | 3/1988 | Middendorf et al. | 435/6 |

FOREIGN PATENT DOCUMENTS 0070959  2/1983  European Pat. Off. ........ 204/299 R

OTHER PUBLICATIONS

Maxam et al., "A New Method of Sequencing DNA", Proc. Nat/Acad. Sci U.S.A., vol. 74, No. 2, pp. 560-564, Feb. 1977.

*Primary Examiner*—Robert J. Warden
*Assistant Examiner*—Stephen C. Wider
*Attorney, Agent, or Firm*—Limbach, Limbach & Sutton

[57] ABSTRACT

Apparatus and method of sequencing nucleic acid molecules, including DNA and RNA molecules. Several copies of the molecules are labeled with a radioactive tracer and divided into separate groups. The groups of molecules are then each chemically cleaved to produce labeled fragments of varying length which terminate in predetermined bases. The groups of fragments are then introduced into separate columns of electrophoresis gel and voltage is applied across the gel to cause subgroups of the fragments to propagate along the columns at a velocity which is a function of the length of the fragments in the subgroup. Radiation detectors are used to detect the subgroups of fragments as they pass a predetermined position along the gel column, and data corresponding to the order in which the subgroups of fragments are detected is stored in a memory. Such data is then used to determine the bases sequence of the molecules.

12 Claims, 7 Drawing Sheets

| C | A | A | G | A | G | A | T | A | C |

| C | A | A | G | A | G | A | T | A | C |

| C | A | A | G | A | G | A | T | A | C |

| C | A | A | G | A | G | A | T | A | C |

| C | A | A | G | A | G | A | T | A | C |

| C | A | A | G | A | G | A | T | A | C |

(PRIOR ART) FIG. 1A

| P32 | C | A | A | G | A | G | A | T | A | C |
| P32 | C | A | A | G | A | G | A | T | A | C |
| P32 | C | A | A | G | A | G | A | T | A | C |
| P32 | C | A | A | G | A | G | A | T | A | C |
| P32 | C | A | A | G | A | G | A | T | A | C |
| P32 | C | A | A | G | A | G | A | T | A | C |

(PRIOR ART) FIG. 1B

VIAL A

| P32 | C | A | A | G | A | G | A | T | A |
| P32 | C | A | A | G | A | G | A |
| P32 | C | A | A | G | A |
| P32 | C | A | A |
| P32 | C | A |

VIAL C

| P32 | C | A | A | G | A | G | A | T | A | C |
| P32 | C |

VIAL G

| P32 | C | A | A | G | A | G |
| P32 | C | A | A | G |

VIAL T

| P32 | C | A | A | G | A | G | A | T |

(PRIOR ART) FIG. 1F

APPARATUS AND METHOD OF ANALYZING NUCLEIC ACID MOLECULES

TECHNICAL FIELD

The present invention pertains generally to the field of apparatus and methods for analyzing the structure of nucleic acid molecules, including DNA (Deoxyribose Nucleic Acid) and RNA (Ribonucleic Acid) molecules and more particularly to determining the nucleotide sequence of such molecules.

BACKGROUND ART

A chemical method of sequencing DNA molecules is disclosed in Maxam, Allan M. and Walter Gilbert, "A New Method for Sequencing DNA," Proc. Natl. Acad. Sci. USA, Vol. 74, No. 2, pp. 560–564, February, 1977, the entire contents of which are incorporated herein by reference. The Maxam/Gilbert method provides for the terminal labeling of several identical DNA strands with radioactive tracers and then breaking the strands at each base into fragments using chemical agents. The relative lengths of the labeled fragments identify the position of the associated base in the strand. For example, the shortest fragment is comprised of a single base, such base being the first base in the sequence. The longest fragment terminates in a base which is the last base of the sequence. The relative lengths of the framents are resolved by electrophoresis thereby enabling the sequence to be ascertained.

Further details of the Maxam/Gilbert sequencing method will be described in connection with FIGS. 1A through 1G. Single-stranded DNA is comprised of four bases, A (Adenine), G (Guanine), C (Cytosine) and T (Thymine). These bases are arranged in the strand to form a sequence. The first step of the sequencing process is to isolate a large number of strands having identical DNA sequences. By way of example, FIG. 1A schematically depicts, in very simplified terms, several DNA strands having the identical sequence CAAGAGATAC. In actual practice, a large number of strands will be isolated. Next, each strand is terminally labeled with a radioactive tracer such as P32, as shown schematically in FIG. 1B.

Once the strands have been labeled, the strands are separated into four groups. Each group is then chemically treated to cleave the base-to-base bonds in a particular way. A first group is placed in a first vial, labeled for convenience as Vial A. Vial A contains chemicals, well known in the art, which, in simplified terms, cause the strands in the vial to cleave the bond at the right of one of the A bases. Thus, the exemplary sequence shown in FIGS. 1A and 1B will produce, with equal probability, the following five different labeled fragments depicted in FIG. 1C: P32CA; P32CAA; P32CAAGA; P32CAAGAGA; and P32CAAGAGATA. Fragments without a P32 tracer are also present in the vial, but will not be detected in the electrophoresis process.

The second group of identically labeled strands is placed in a second vial, labeled Vial C, which contains chemicals, well known in the art, which cause the strands in the vial to break the sequence at the right of one of the C bases. The following two labeled fragments will be produced, as shown in FIG. 1D: P32C; and P32CAAGAGATAC.

The third and fourth groups of strands are placed in third and fourth vials, labeled Vials G and T, respectively. Vials G and T contain chemicals, which cause the strands in the vials to break the bonds to the right of G and T bases, respectively. FIG. 1F depicts the following two Vial G labeled fragments which result: P32CAAG and P32CAAGAC. FIG. 1F shows the single Vial T labeled fragment which is produced: P32 CAAGAGAT.

The tagged P32 fragments are then separated by size using conventional electrophoresis. A separate gel track, typically one meter in length is provided for each of the four groups of fragments. Each track has a square well at the top for the initial placement of the DNA fragments. A uniform voltage is applied across the length of the gel, causing the fragments to travel along the gel track with a velocity approximately according to the following equation:

$$V = (K)(V)(-\log(N) + A) \tag{1}$$

where K and A are positive constants, V is the applied voltage and N is the number of bases contained in the fragment.

It can be seen from equation (1) that the velocity of the fragments is a non-linear function of the applied voltage, with the smaller fragments traveling at the higher velocities.

After an elapsed time interval, the fragments will be distributed in subgroups along the length of each of the parallel gel tracks in accordance with the length of the fragments in the subgroup. The gel is then removed and exposed to photographic paper to form an autoradiograph. The paper is then developed, thereby producing a visual image which shows the relative position of the subgroups of fragments along the length of the gel.

FIG. 1G illustrates a developed exposure which was made for the FIG. 1A DNA sequence in accordance with the previously-described autoradiography procedure. The tagged fragments were initially positioned at the top of the exposure, with the Vial A track being positioned along the left edge of the exposure, followed by the Vial C, G and T tracks.

The subgroup comprised of the smallest fragments will be comprised of the single base adjacent the P32 label of the original strand as shown in FIG. 1D. This subgroup of fragments will have traveled the greatest distance, as indicated by equation (1). Since the smallest fragment came from Vial C, the first base of the sequence is a C base. The next smallest subgroup of fragments will be comprised of fragments having two bases, including first base C followed by a second base. As can be seen from FIG. 1G, the next smallest (fastest) fragment came from Vial A, therefor the second base of the sequence is an A. This process is continued for each of the remaining eight bases. The final sequence is P32CAAGAGATAC which corresponds to the FIG. 1A sequence.

It was previously assumed that vials G and T originally contained fragments which terminated in G at T bases, respectively. In actual practice and in accordance with conventional chemical processes, vial G will probably contain fragments which terminate in both G and A fragments and vial T will contain fragments which terminate in both T and C fragments. In that event, fragments terminating in T bases can be uniquely identified by observing the presence of fragments at a particular position on the exposure along the vial T track and the absence of fragments at the corresponding position along the C vial track. The position of fragments terminating in G bases can be uniquely determined in a similar manner.

Conventional gel electrophoresis utilizing autoradiography is quite time consuming and very labor intensive. The electrophoresis gel must be carefully prepared so as to provide a uniform structure through which the fragments pass. Any nonuniformity may result in sequencing errors. A gel approximately 1 meter long is capable of determining roughly 100 bases of a sequence. For a DNA sequence of 1000 bases, the procedure requires 5-10 gel runs lasting 8 to 16 hours. After each gel is run, the gel must be separated from its supporting glass plate and exposed for 8 to 48 hours with photographic paper. After the DNA sequence is obtained, it is typically manually entered into a computer for further analysis. The entire procedure, which must be performed by a skilled technician, requires at least a week of applied time and an elapsed time of several weeks. In addition, evaluation of the autoradiation photographs and entry of the sequence into a computer is susceptible to human error.

Some attempts have been made to overcome the above-noted limitation of the Maxam/Gilbert sequencing procedure. For example, it is believed the automated imaging techniques have been utilized to analyze the autoradiation photographs. Despite such advances, the principal shortcomings of the Maxam/Gilbert procedure remain.

The present apparatus and method for DNA and RNA sequencing overcomes the limitations of the Maxam/Gilbert procedure. The time required to obtain a DNA sequence is greatly reduced. Moreover, the procedure can be carried out by persons having limited training. In addition, overall accuracy is improved inasmuch as it is not necessary to interpret a photograph and manually enter data into a computer. These and other advantages of the subject invention will become apparent to those having average skill in the art upon reading the following Best Mode For Carrying Out The Invention.

DISCLOSURE OF THE INVENTION

Apparatus and method for analyzing the structure of a nucleic acid molecule, such as a DNA or RNA molecule, is disclosed. Several copies of the molecule to be analyzed are prepared and preferably labeled with a radioactive tracer. The copies are then separated into four groups and each group is chemically cleaved to produce labeled fragments which terminate with predetermined bases using conventional and well-known chemistry. In the case of DNA and RNA molecules, there are preferably four separate groups of fragment.

A separate electrophoresis gel channel is provided for each of the groups of labeled fragment. The gel channels are typically contained in separate elongated glass tubes. A voltage is applied across each of the gel channels and the fragment are introduced into the channels. The fragments propogate along the length of the channel in accordance with well-known principles of electrophoresis with the smaller fragments moving at greater velocities.

A detector is located at a predetermined position adjacent the gel channels, downstream from the point where the fragments were introduced. In the event radioactive tracers are used, the detector is a radiation detector. Light detectors would be used in the event the tracers are fluorescent. Once the fragments have reached the detectors, the fragments will have become separated into subgroups in accordance with the length of the fragments because of the velocity differences. When the subgroups pass a detector, the detector outputs a signal. Data corresponding to the signal are preferably then stored in a memory for further processing. The order in which the respective subgroups of labeled fragments are detected may then be analyzed to determine the base sequence of the molecule.

BRIEF DESCRIPTION OF THE DRAWINGS

FIGS. 1A-1G schematically illustrate the previously-noted Maxam/Gilbert method of sequencing DNA.

BEST MODE FOR CARRYING OUT THE INVENTION

Figures 1C, 1D, 1E, 1G:
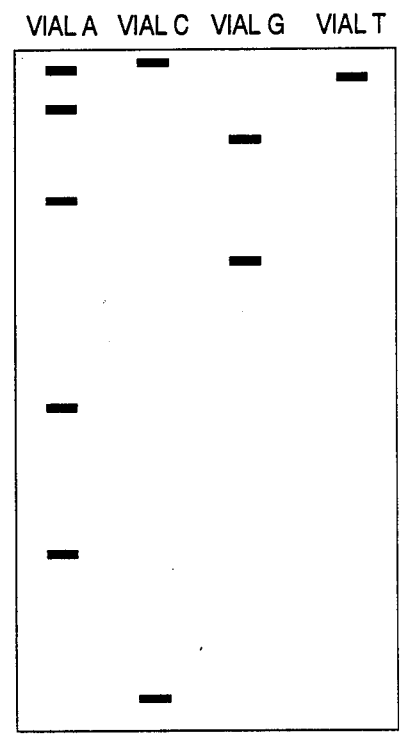
Figure 2:
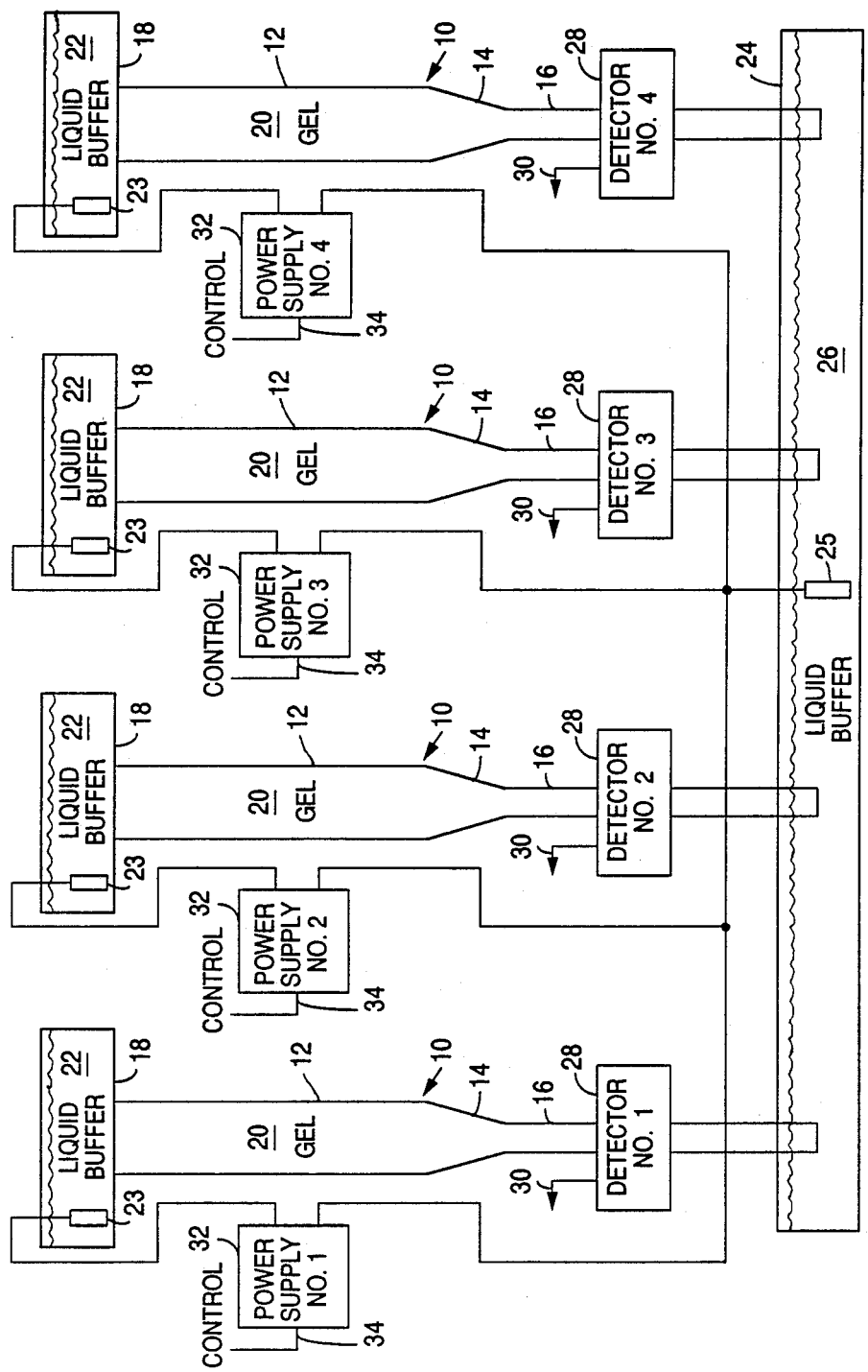
FIG. 2 is a schematic diagram of the four electrophoresis columns and associated apparatus of the subject invention.

Referring again to the drawings, the electrophoresis components of the subject invention depicted in FIG. 2 include four glass tubes, each generally designated by the numberal 10. Tubes 10 are preferably maintained in a vertical position by a suitable support structure (not shown).

Tubes 10 each include a relatively long, wide section 12, a relatively short, narrow section 16 and a tapered transition section 14 intermediate sections 12 and 16. Wide section 12 is typically on the order of 50 cm in length with the narrow sections and transition sections typically being on the order of 5 cm and 1 cm, respectively. The interior cross-sectional area of narrow section 16 is preferably approximately one-tenth that of wide section 12.

Tubes 10 are filled with a gel 20 such as used in conventional electrophoresis processes. A polyacrylamide gel has been found suitable for the present application. A separate reservoir 18 is positioned above each tube 10 and is in communication with the interior of the tubes. Reservoirs 18 contain a electrically conductive liquid buffer 22 such as tris-acetate, tris-phosphate or tris-borate. The lower ends of each of tubes 10 is disposed in an elongated reservoir 24 which is filled with a liquid buffer 26 similar to buffer 22.

A separate power supply 32 is provided for each tube 10. Supplies 32 are conventional power supplies having an adjustable output voltage which may be varied between approximately 0 and 5,000 voltage in response to control signals supplied to line 34, such line being coupled to the control input of the associated supply. The power supplies are capable of supplying current in excess of 200 ma.

The positive output of power supplies 32 are each connected to separate electrodes 23 which are disposed in the liquid buffer 22 of reservoirs 18. The negative output of the supplies are connected to a single electrode 25 disposed in lower reservoir 24. The conductive buffer solutions serve to electrically couple the outputs of the power supplies to the upper and lower surfaces of gel 20 contained in the tubes.

As will be subsequently described in greater detail, DNA fragments, or fragment from other varieties of nucleic acid such as RNA, having radioactive labels, propagate down the length of tubes 10 through gel 20 by electrophoresis. Radiation detectors 28 are provided for each tube 12 for detecting the passage of the labeled fragments. Each time a beta emission is detected in the region of the detector, a digital output pulse is provided on output line 30.

Figure 3:
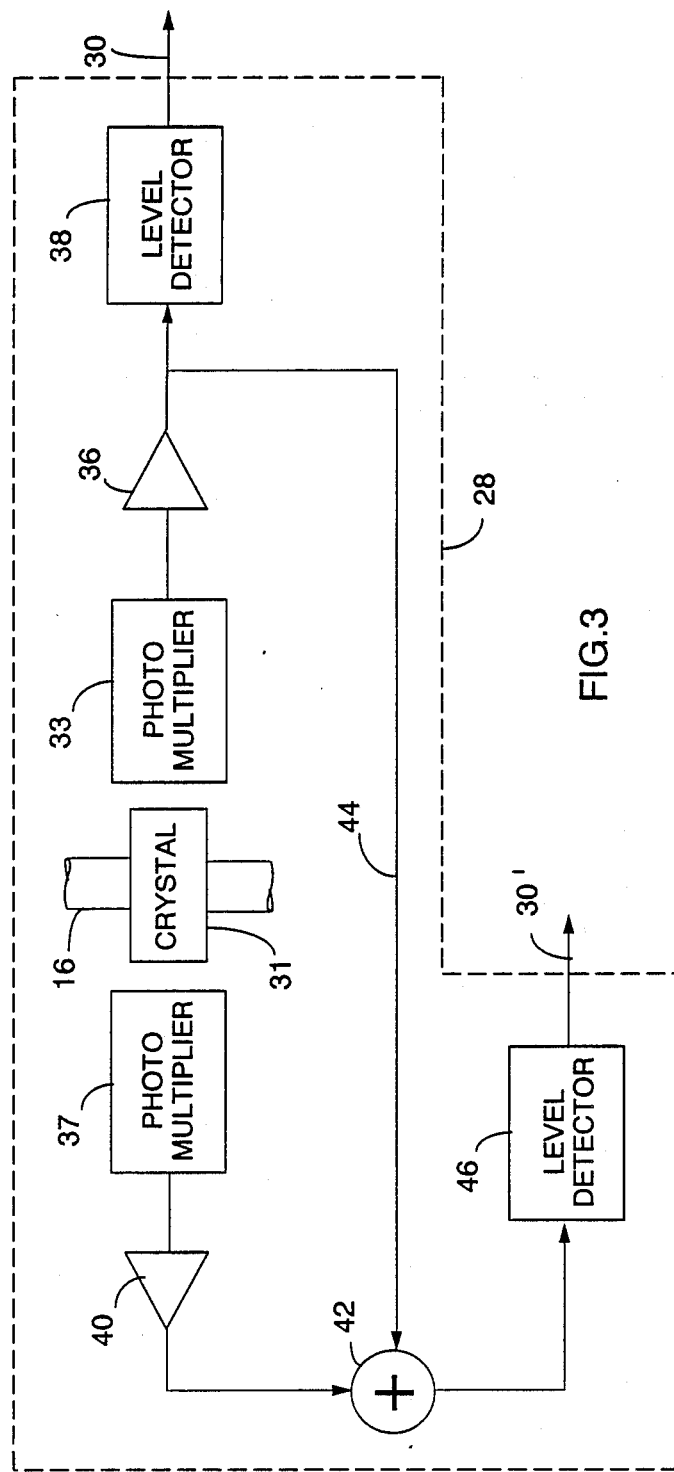
FIG. 3 is a simplified block diagram of one of the four identical radiation detectors of the subject invention.

Referring now to FIG. 3, detail of the construction of an exemplary radiation detector 28 may be seen. Detectors 28 include a conventional plastic phosphor scintillation crystal 31 which extends around the narrow section 16 of each of tubes 10. Crystal 31 is in the general form of a cube having a central aperture through which tube 10 extends. When a labeled fragment in gel 20 passes through the aperture, the emitted beta particles strike crystal 31 causing the crystal to scintillate. The probability of detecting such randomly produced beta particles is increased by increasing the dimension of the crystal along the length of the tube. However, the increased height of the crystal reduces the capability of the detector to resolve the position of the fragment when the emission is detected. A compromise crystal height of approximately 0.5 cm has been found to be optimum for the present application.

Detectors 28 each further include a conventional photo-multiplier 33 which is optically-coupled to crystal 31. Multiplier 33 detects the light bursts produced within crystal 31 when the crystal scintillates and produces a low level electrical output signal in response thereto. The signal is amplified by a low-noise amplifier 36 having a gain of approximately 100 to 300. Amplifier 36 also preferably includes conventional filtering circuitry which integrates the multiplier output signal for approximately 1000 nanoseconds and then differentiates for 100 nanoseconds.

The output of amplifier 36 is coupled to a level detector 38. Detector 38 includes a monostable or single shot circuit which produces a single digital pulse on output line 30 when the output of amplifier 36 exceeds a predetermined threshold level.

Because of the noise inherent in photo-multiplier 33 and amplifier 36, it is possible that an output pulse will be produced on line 30 even in the absence of a beta emission. Accordingly, an optional second photo-multiplier circuit 37 may be provided which is also optically coupled to crystal 31. In that event, level detector 38 is deleted. The output of the second photo-multiplier 37 is coupled to a second low noise amplifier 40, similar to amplifier 36 on line 44. The outputs of both amplifiers 36 and 40 are connected to a conventional summing amplifier 42 which sums the two signals together and produces an output which is coupled to a level detector 46, similar to detector 38. The threshold level of detector 46 is selected such that a simultaneous output from both amplifier 36 or amplifier 40 is required to produce a digital output pulse on line 30. Thus, background noise, which is likely to cause one, but not both, of amplifier 36 and 40 to produce an output, will not cause a pulse to be produced on line 30'.

Figure 4:
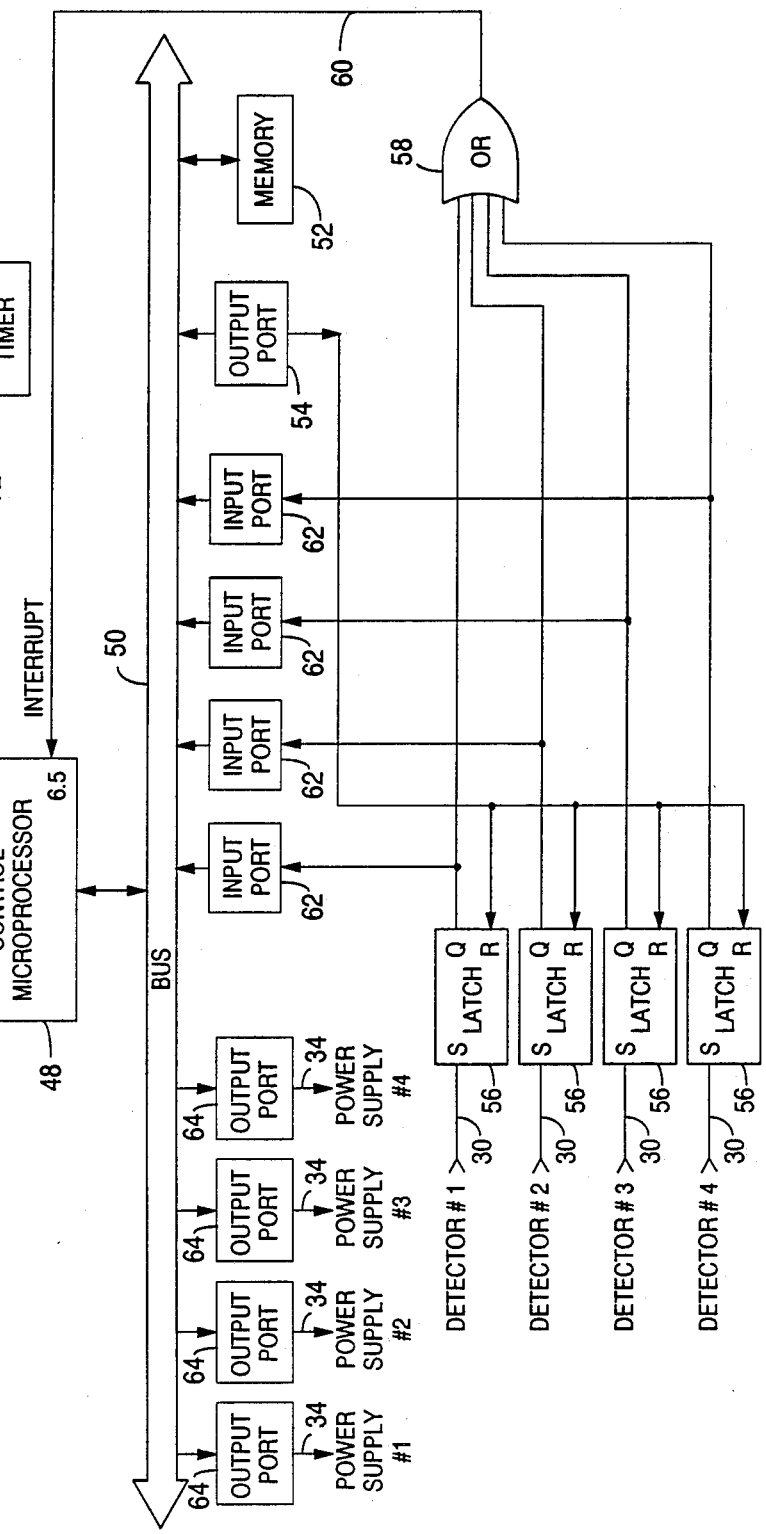
FIG. 4 is a simplified block diagram of the data processing apparatus of the subject invention.

Details of the signal processing aspect of the subject apparatus are shown in the block diagram of FIG. 4. A control microprocessor, represented by block 48, is coupled to a main bus 50. A microprocessor manufactured by Intel having the designation 8085 has been found suitable for the present application although there are many other devices which could also be used. Microprocessor 48 is under program control by a program stored in a memory 52 also coupled to the bus. Memory 52 may be a Read Only Memory (ROM) or an Erasable Programmable Read Only Memory (EPROM), both of which are non-volatile.

The outputs of the four radiation detectors 28 (FIG. 2) on lines 30 are coupled to the Set inputs of separate latch circuits 56. The outputs of the latch circuits are connected to separate input ports 62 which interface with bus 50. The Reset inputs of latches 56 are connected to a common output port 54 which is also coupled to bus 50. Four output ports 64 are further coupled to bus 50 and provide separate control signals on lines 34 for independently controlling the magnitude of the output voltage of power supplies 32 (FIG. 2).

The outputs of latches 56 are further connected to the inputs of a four-input OR gate 58. The output of gate 58 is connected to the 6.5 interrupt input of the Intel 8085 processor 48 by way of line 60. An interrupt timer circuit, represented by block 70, produces a 7.5 interrupt signal one line 72 for processor 48 by way of line 72.

Control processor 48 is further in communication with a microcomputer 68 through an interface circuit 66. As will be subsequently described in greater detail, control microprocessor 48 is generally dedicated to collecting data provided by the four radiation detectors with microcomputer 68 serving to process and record such data.

Having described the overall construction of the subject sequencing apparatus, operation of the apparatus will now be given. The sequencing of DNA will be used as an example, it being understood that the subject invention can be used to analyze the structure of other varieties of nucleic acids, including RNA. DNA fragments are first prepared, as previously set forth in connection with the discussion associated with FIGS. 1A–1G. It should be noted that the chemical process for cleaving the DNA strand is not actually as selective as previously described. For example, although vial A will primarily contain fragments terminating with A bases, there will also be a significant number of fragments terminating in the other three bases. In addition, as will be subsequently explained, it may be desirable to add a small quantity of labeled fragments terminating with each of the four bases to each vial.

The contents of each of the four vials are then introduced into the top layer of gel in respective ones of the four tubes 10. Because of the potential produced across the length of the column of gel 20, the fragments will propogate towards the bottom of the column in accordance with the well known principles of electrophoresis. As previously described, the rate of propogation is a function of the size of the fragments, with the subgroups of smaller fragments moving at a greater velocity than the subgroups of the larger fragments.

As the fragments propogate along the length of the tubes, the fragments become separated into subgroups in accordance with the length of the fragments. Since there are ten different fragment lengths (ten bases) in the example of FIGS. 1A-1F, there will be ten separated subgroups of fragments in each tube 10. The tube containing the contents of vial C, for examples, will have two large subgroups of fragments (P32C and P32CAAGAGATAC) and eight small subgroups. The number of fragments in each subgroup and the P32 radioactive label are selected such that the large subgroups produce intense radiation bands which emit approximately 200 beta particles per minute. Such emissions result in a detector output of 200 counts per minute (cpm). The small subgroups are selected to produce weak radiation bands which generate approximately 50 cpm. It may be necessary to add labeled fragments terminating in each of the ten bases to each vial in order to enhance the weak radiation bands.

An alternative method of synchronization is to utilize chemical reactions which produce the following four groups of fragments terminating in the following bases: A+C+G; A+C+T; A+G+T and C+T+G. The four groups can be run in separate columns. There are always three bands in each column to be aligned and the fourth band can be aligned by analysis. The fragment groups may be prepared by mixing the results of two or more known chemical reactions in the event such groups cannot be directly produced.

It is important that the radiation bands be separated from one another a sufficient distance for the detectors 28 to resolve the different bands. A band separation of 1.0 cm has been found to be suitable when a detector having a crystal height of 1.0 cm is used. The desired separation can be achieved utilizing glass tube of relatively great length having a constant cross-section where the intensity of the electric field is uniform throughout the length of the gel column. However, it is preferable to use tubes as depicted in FIG. 2 having a relatively wide upper section 12 and a relatively narrow lower section 16 with an intermediate tapered section. The intensity of the electric field in narrow section 16 is greater then that of the wide section by approximately a factor of ten since the ratio of the cross-sectional area of the wide section is ten times that of the narrow section. Accordingly, the velocity of the fragments substantially increase when the fragments pass from the wide section to the narrow section, thereby increasing the subgroup separation a sufficient amount so that the radiation bands may be resolved by the detectors. In addition, the reduced cross-sectional area increases the probability of detecting a beta particle emission since there is a smaller amount of gel which the particles must penetrate before entering the crystal.

It is desirable to maximize the velocity of the fragments through the gel in order to reduce the time required to complete the sequencing process. However, if the velocity is too great, the probability that a radiation band will not be detected as it passes through the detectors 28 is increased. If the potential applied across the gel is adjusted to achieve the desired velocity for the short fragments, the velocity of the larger fragments will be substantially reduced. It is preferable to periodically increase the potential during the sequencing process so as to maintain a constant fragment velocity. A constant fragment velocity of approximately 1.0 cm per second through narrow section 16 has been found to be acceptable.

The desired constant velocity is maintained by independently controlling each of the four adjustable power supplies 32. In addition, the adjustable power supplies permit the fragment subgroups in each tube to be synchronized with one another. Synchronization is achieved when an intense radiation band is detected in one column at approximately the same time weak bands are detected in the other three columns. If the bands do not occur substantially simultaneously, the potential is across the gels are adjusted, as required, to resynchronize the bands.

The first step in carrying out the sequencing procedure is to first introduce the fragments from the four vials into respective ones of the glass tubes. The operator then enters initial setup information into microcomputer 68 using a conventional keyboard (not depicted) as indicated by block 90 of the FIG. 8 flow chart which illustrates the operation of microcomputer 68. Such information includes, for example, the approximate number of bases in the strand to be sequenced. Also, information regarding the chemistry used in producing the fragments in the four vials may be entered. In the example given, the chemistry for cleaving the DNA strands generally produces fragments terminating in one of four bases. However, other chemical procedures can be used to produce different fragment groupings. By way of example, another chemical cleaving process commonly used in conventional DNA sequencing produces a first group of fragments terminating primarily in A bases and secondarily in G bases. A second separate group of fragments is produced terminating primarily in G bases and secondarily in A bases, with a third separate group of fragments being produced which terminates in C bases and a fourth separate group of fragments being produced terminating in both C and T bases. It can be seen that sufficient information is provided in the four groups to uniquely determine the type of base. By way of example, if a radiation band is detected in a gel column containing the fourth group of fragments, but not in the column containing the third group, it is known that the detected fragments terminate in base T.

Figure 8:
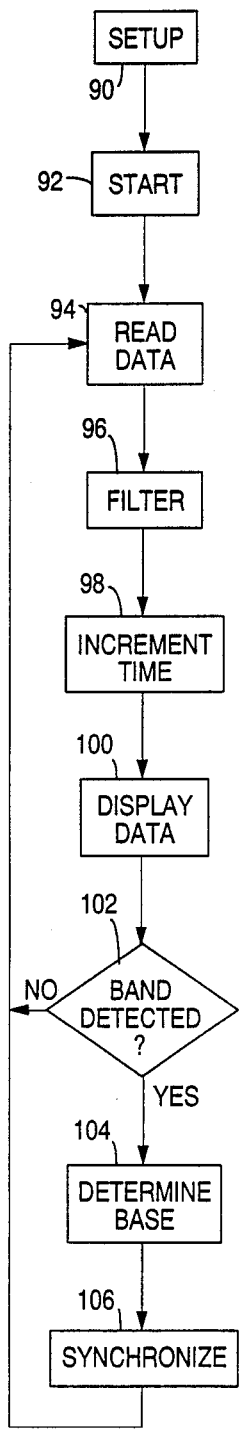
FIG. 8 is a flow chart generally illustrating the operation of the microcomputer of the FIG. 4 data processing apparatus.

Once the setup procedure has been completed, a Start command is forwarded from microcomputer 68 to control microprocessor 48 through interface 66, as indicated by block 92 of the FIG. 8 flow chart. Microcomputer 68 is also capable of issuing a Stop command and a Voltage Adjust Command, these being the three primary microcomputer commands.

Figure 5A:
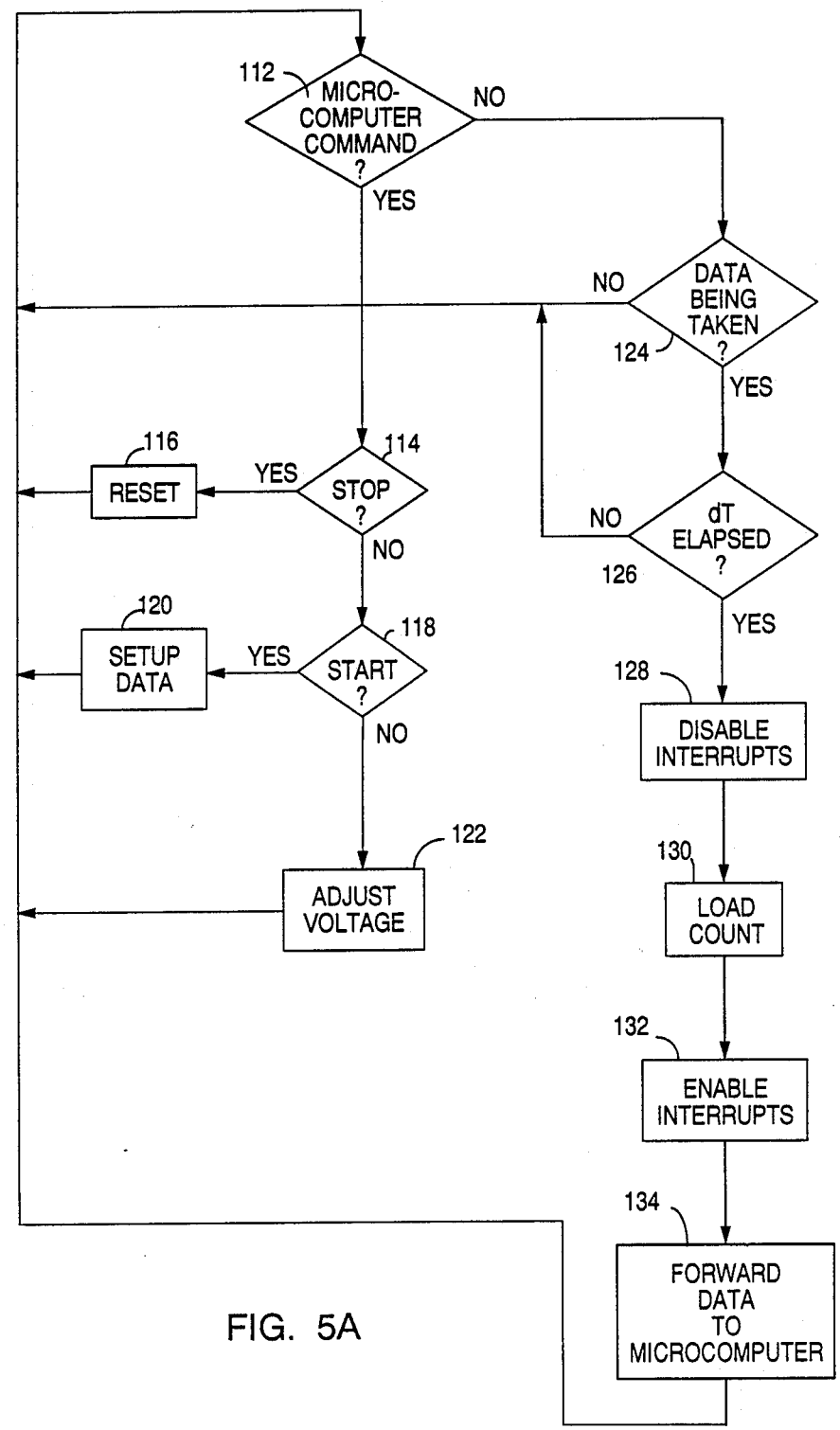
FIGS. 5A-5C are flow charts generally illustrating the operation of the control microprocessor of the FIG. 4 data processing apparatus.

Referring now to the FIG. 5A flow chart which illustrates the operation of control microprocessor 48, as represented by element 112 the microprocessor periodically determines whether microcomputer 68 has issued one of the three primary commands by way of interface 66. As indicated by elements 114 and 118 of the flow chart, a determination is made as to whether the command was either a Stop or a Start. Since a Start command had issued, the microprocessor will then initialize the system for taking data as indicated by block 120. The sequence will then return to element 112 at which time a determination will be made as to whether another command from the microcomputer has issued. Since no command will have been given, the program will proceed to element 124 where it is determined that data from the detectors are in the process of being recorded.

Data from the detectors are accumulated over a time period dT, with the period typically being on the order of 10 seconds. When a beta emission is detected by one of the detectors, a digital pulse is produced on the associated output line 30. The emission may be the result of background radiation, an intense radiation band caused by the passage of a large subgroup of labeled fragments past the detector or a weak radiation band caused by the passage of a small subgroup of labeled fragments.

A digital pulse from any of the detectors causes the associated latch 56 to set. The latch output causes the output of OR gate 58 to go high thereby producing a 6.5 interrupt for control microprocessor 48. In addition, the latch output is forwarded to the associated input port 62.

Figure 5C:
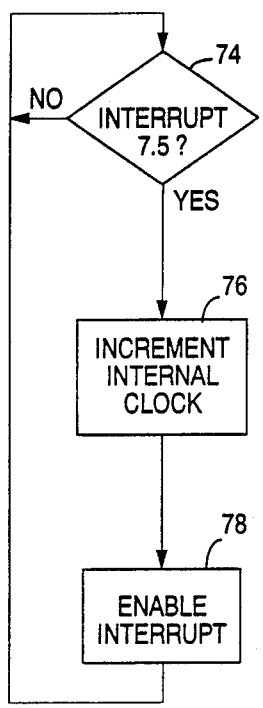
Figure 5B:
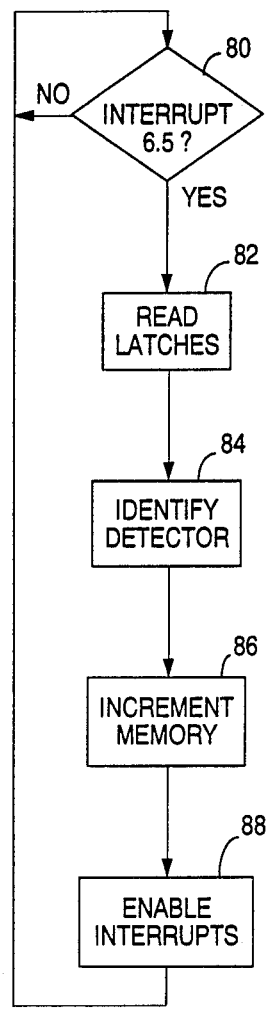

Referring now to FIG. 5B flow chart, the sequence for processing the 6.5 interrupts is depicted. When an interrupt is detected, the interrupt is processed and additional interrupts are disabled. Interrupt processing typically requires only approximately 100 microseconds, therefore, it is unlikely that a significant number of beta emissions will be missed during the processing.

As indicated by element 80 and block 82, when the interrupt is detected, the status of each of the latches 56 is read through input ports 62. Microprocessor 48 has internal memory locations associated with each of the four detectors which accumulate the number of output pulses produced by each detector during a time period dT. Depending upon which latch was set, the identity of the particular detector which produced the output pulse is then determined as indicated by block 86. The digital value stored in memory location associated with the detector is incremented, as represented by block 86, and interrupts are then enabled as indicated by block 88.

Returning again to FIG. 5A flow chart, data continues to be taken throughout the remainder of time period dT, as indicated by elements 124 and 126. Once the time period has elapsed, the count totals from the four memory locations are loaded into buffer registers (not depicted), as shown by block 130 and the interrupts are enabled, as represented by block 132. Next, a command is sent to microcomputer 68 through interface 66 indicating that the four groups or channels of data are about to be forwarded to the microcomputer. The four channels of data are then forwarded to the microcomputer as represented by block 134. The program then returns to element 112 and the sequence is repeated every dT time period.

Control microprocessor 48 is implemented to provide an internal clock for measuring time interval dT. Interrupt timer 70 (FIG. 4), which produces an output signal approximately once every one millisecond, is coupled to the 7.5 interrupt input of microprocessor 48. As shown in the 7.5 interrupt processing sequence of the FIG. 5C flowchart, when the microprocessor detects a 7.5 interrupt, further interrupts are disabled. Next, as indicated by element 74 and and block 76, the internal microprocessor clock is incremented followed by the reenabling of interrupts as represented by block 78.

Returning to FIG. 8, once the four channels of data have been received by microcomputer 68 from the control microprocessor, the data associated with each of the detectors are filtered as indicated by block 96. The purpose of filtering is to detect the presence of intense and weak radiation bands and to distinguish such bands from background radiation. Filtering also serves to distinguish intense bands from weak bands.

Filtering is carried out utilizing digital filtering techniques. A location filter is first used to filter the input data so as to provide a relatively smooth curve having a peak which correspond to the time in which a possible radiation band was detected. The input data are also filtered by a rate filter to determine the radiation rate at the time the band was detected. The radiation rate is used to distinguish between radiation bands and background radiation and between intense and weak radiation bands.

Figure 6:
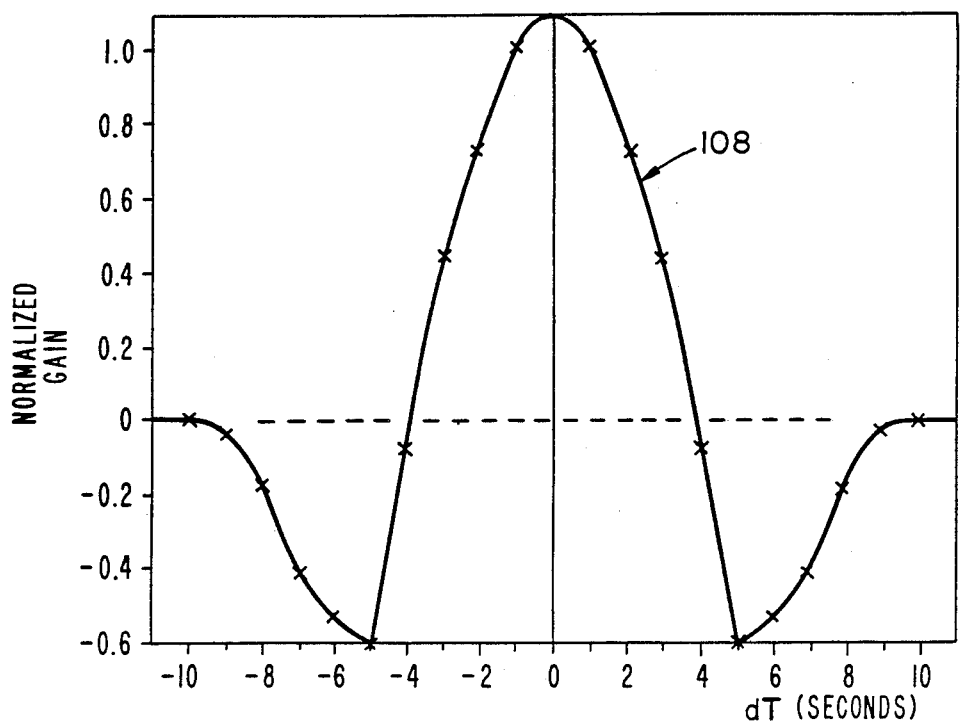
FIG. 6 is a graphical illustration of the transfer characteristics of the digital location filter of the subject invention.
Figure 7:
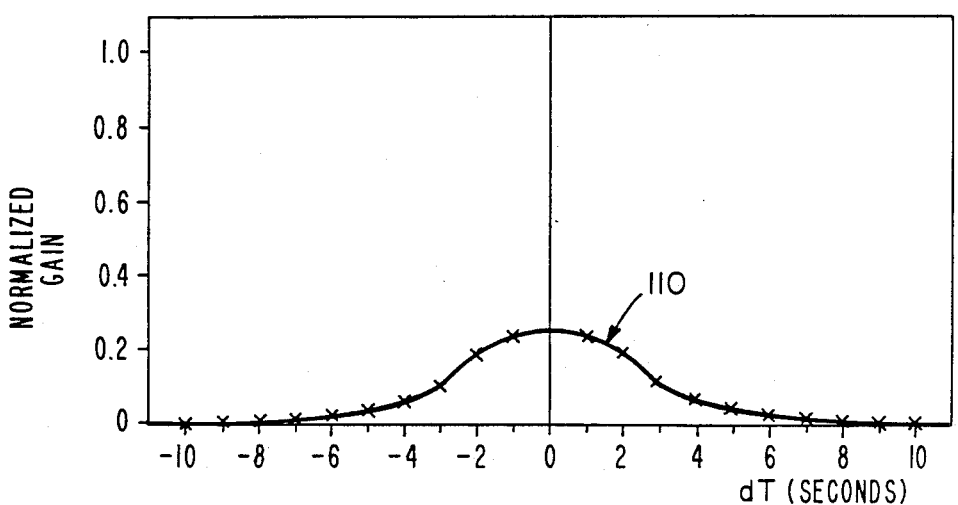
FIG. 7 is a graphical illustration of the transfer characteristics of the digital rate filter of the subject invention.

The digital filters are implemented utilizing look-up tables which are stored in the microcomputer memory. Each table contains twenty different filter values or constants which define the filter transfer characteristics. The preferred twenty values stored for the location filter, in normalized form, are plotted on the graph of FIG. 6, with the points on the graph being connected together to form a transfer characteristic curve 108. FIG. 7 shows the values stored in the rate filter look-up table, which are connected together to form curve 108.

Filtering is accomplished by multiplying the twenty stored filter values together with data taken for twenty consecutive time periods dT. The multiplication is repeated each time a new set of data is forwarded to the computer. By way of example, the data forwarded after the first time interval are multiplied by the filter value plotted on the FIG. 6 graph at dT=10, with the subsequent nineteen sets of data being simultaneously multiplied with the value plotted at dT=9 through dT=-10. During the next time interval, the input data are shifted one location so that the data of the second time interval will be multiplied with the filter value of dT=10 and the most recently inputted data will be multiplied with the filter value plotted at dT=-10.

The peak of the filter output data from the location filter corresponds to the time in which a potential radiation band passed through the associated detector. The inputted data are also processed by the rate filter in a similar manner to determine the radiation rate at the time the potential band passed the detector, as determined from the output of the location filter.

Microcomputer 68 is provided with an internal clock so that the relative times that the four channels of data are received from control microprocessor 48 may be determined. Referring back to the FIG. 8 flow chart, once the four channels of data for a particular time interval dT have been filtered, the internal clock is incremented, as indicated by block 98. The filtered data may then be displayed, if desired, on a CRT display (not shown) as represented by block 100.

If the radiation rate at the time the potential radiation band was detected is below a predetermined value, it is assumed that the radiation was caused by background radiation rather than a radiation band. In the present example, where intense and weak radiation bands nominally produce 50 cpm and 200 cpm, respectively, any radiation rate less than 20 cpm is treated as background radiation. In that event, the microcomputer program will loop back to block 94, to read further incoming data, as indicated by element 102. If the radiation rate is greater than 20 cpm, but less than 100 cpm, it is assumed that a weak band was detected. If the measured rate is greater than 100 cpm, it is assumed that an intense radiation band was detected.

If a radiation band has been detected, the program will proceed to block 104, at which time a determination is made as to which base was detected. In the present example, assuming that the system is synchronized, one of the detectors will detect an intense band while the remaining three detectors will detect weak radiation bands. Since the chemistry is such that each tube primarily contains fragments terminating in one of the four bases, the base associated with the column which produced the intense band will be the base at that point in the sequence.

Synchronization is desirable because, among other things, the processing of the data is simplified. For example, when the system is synchronized, it is not necessary to record the actual times that radiation bands are detected since the base sequence of the molecule will be identical to the order in which the bands are detected. It would be possible to determine the base sequence if the system were not synchronized, provided the absolute time in which each of the bands is detected is recorded. Such recordation would be performed automatically by microcomputer 68.

As previously noted, one of the purposes of the weak radiation bands is to facilitate synchronization. If synchronization is not desired, the weak bands may be ignored. If synchronization is to be achieved, an appropriate Adjust Voltage command is sent to control mircoprocessor 48 to maintain synchronization, as indicated by block 106.

The Adjust Voltage command includes data for independently controlling each of the power supplies. Referring to the FIG. 5A flow chart, when control microprocessor 48 detects that a microcomputer command has been sent, a determination is made that the command is neither a Stop nor a Start command, as indicated by elements 114 and 118. Accordingly, the program will advance to block 122 where the command will be decoded as an Adjust Voltage command. The decoded data for each power supply will then be forwarded to the respective supply by way of output ports 64. By way of example, if a weak band in one column is lagging the one intense band and two weak bands of the other three columns, the power supply associated with the lagging column will be increased slightly to increase the velocity of the fragment. The magnitude of the increase in voltage will be selected in accordance with well known principles of feedback control system design.

The Voltage Adjust commands are also used to maintain the velocity of the radiation bands at the desired 1.0 cm per second past the detectors. The velocity may be determined by measuring the time intervals between the detection of radiation bands and is be corrected by issuing appropriate Voltage Adjust commands, also in accordance with principles of feedback control system design.

The above-described sequencing process continues during subsequent time intervals dT until the last subgroup of labeled fragments has been detected. If no radiation bands are detected for a predetermined time period, it is assumed that the sequence has been completed. Microcomputer 68 then issues a Stop command to control microprocessor 48 which, as indicated by element 114 and block 116 of the FIG. 5A flow chart, cause the system to be reset. The sequence data are preferably recorded, as it is processed, in some form of non-volatile memory storage medium such as floppy-disks or the like. The data can then be further analyzed without the necessity of manually entering the data into the computer.

Thus, a novel apparatus and process for sequencing nucleic acids have been disclosed. Although a preferred embodiment has been described in some detail, it is to be understood that various changes can be made by those skilled in the art without departing from the spirit and scope of the subject invention as defined by the appended claims.

We claim:

1. A method of analyzing the structure of nucleic acid molecules comprising the following steps:
   providing several copies of said nucleic acid molecule to be analyzed
   separating said copies into separate groups of molecule fragments;
   introducing said groups into separate electrophoresis gel channels;
   applying a voltage across said gel channels so that each of the groups becomes separating along the channels into subgroups of the fragments, with the fragments which comprise one of the subgroups having the same number of bases.
   detecting when an individual one of the subgroups passes a predetermined position along said gel channels and producing an output signal in response thereto; and
   storing data which represent said signals.

2. The method of claim 1 wherein said voltage applied across said gel channels is periodically adjusted to maintain a substantially constant fragment velocity when said subgroups pass said predetermined position.

3. The method of claim 1 further comprising the step of labeling said molecule fragments with a radioactive tracer and wherein said detecting step is carried out utilizing a radiation detector.

4. The method of claim 1 wherein said gel channels include a first section where said groups of molecule fragments are introduced followed by a second section at said predetermined position and wherein, subsequent to said step of applying a voltage, said method includes the additional step of increasing the velocity of said subgroups of molecule fragments when said subgroups exit said first section and enter said second section so as to increase the separation between said subgroups of molecule fragments at said predetermined position.

5. The method of claim 4 wherein said step of increasing the velocity of said subgroups of molecule fragments is carried out by providing said electrophoresis gel channels having said first sections with a relatively large cross-sectional area and said second sections with a relatively small cross-sectional area.

6. A method of analyzing the structure of DNA molecules comprising the following steps:
   providing several copies of strands of DNA molecules to be analyzed;
   labeling said copies with a tracer;
   separating said copies into at least three different groups;
   chemically cleaving said groups in a predetermined manner into fragments;
   introducing said fragmented groups into separate electrophoresis gel channels; applying a voltage across said gel channels;
   detecting said tracer as groups of said fragments having the same number of bases pass a predetermined position along said gel channel;
   producing a separate output signal for each of said gel channels in response to said detected fragments; and
   storing data which represent said output signals.

7. The method of claim 6 wherein said voltage across each of said gel channels is independently controlled and said tracer is a radioactive tracer.

8. A method of analyzing the structure of nucleic acid molecules comprising the following steps:

providing fragments of said nucleic acid molecule to be analyzed, the fragments having a varying number of bases;

introducing the fragments into an electrophoresis gel channel;

applying a voltage across said gel channel so that the fragments become distributed along the channel into separate groups of fragments having the same number of bases;

detecting the passage of an individual one of the groups across a predetermined position on said one gel channel and producing an output signal in response thereto; and storing data which represent said output signal.

9. The method of claim 8 wherein said voltage applied across said gel channel is periodically adjusted to maintain a substantially constant fragment velocity when said groups of fragments pass said predetermined position.

10. The method claim 8 further comprising the step of labeling said molecule fragments with a radioactive tracer and wherein said detecting step is carried out utilizing a radiation detector.

11. The method of claim 8 wherein said gel channel includes a first section where said molecule fragments are introduced followed by a second section at said predetermined position and wherein, subsequent to said step of applying a voltage, said method includes the additional step of increasing the velocity of said molecule fragments when said fragments exit said first section and enter said second section so as to increase the separation between said groups of molecule fragments at said predetermined position.

12. The method of claim 11 wherein said step of increasing the velocity of said molecule fragments is carried out by providing said electrophoresis gel channel having said first section with a relatively large cross-sectional area and said second section with a relatively small cross-sectional area.

* * * * *